United States Patent [19]

Haag et al.

[11] Patent Number: 5,237,120
[45] Date of Patent: Aug. 17, 1993

[54] DOUBLE BOND ISOMERIZATION OF OLEFIN-CONTAINING FEEDS WITH MINIMAL OLIGOMERTIZATION USING SURFACE ACIDITY DEACTIVATED ZEOLITE CATALYSTS

[75] Inventors: Werner O. Haag, Lawrenceville; Roland H. Heck, Pennington, both of N.J.; Jose G. Santiesteban, Yardley, Pa.; David S. Shihabi, Pennington, N.J.

[73] Assignee: Mobil Oil Corporation, Fairfax, Va.

[21] Appl. No.: 813,717

[22] Filed: Dec. 27, 1991

[51] Int. Cl.$^5$ ............................................. C07C 5/25
[52] U.S. Cl. .................... 585/666; 585/664; 502/62; 502/64
[58] Field of Search ............... 585/666, 664; 502/62, 502/64

[56] References Cited

U.S. PATENT DOCUMENTS

| | | | |
|---|---|---|---|
| 2,804,490 | 8/1957 | Belden | 260/683.4 |
| 3,178,365 | 4/1965 | Miale | 585/666 |
| 3,800,003 | 3/1974 | Sobel | 260/683.49 |
| 4,002,697 | 1/1977 | Chen | 260/671 |
| 4,100,215 | 7/1978 | Chen | 260/671 |
| 4,101,595 | 7/1978 | Chen et al. | 260/668 |
| 4,520,221 | 5/1985 | Chen | 585/517 |
| 4,568,786 | 2/1986 | Chen et al. | 585/517 |
| 4,727,203 | 2/1988 | Hamilton | 585/670 |
| 4,749,819 | 6/1988 | Hamilton, Jr. | 585/329 |
| 4,870,038 | 9/1989 | Page et al. | 502/62 |
| 4,918,255 | 4/1990 | Chou et al. | 585/331 |
| 4,982,031 | 1/1991 | Chen | 585/624 |
| 5,015,361 | 5/1991 | Anthes et al. | 208/111 |

FOREIGN PATENT DOCUMENTS 0247802 12/1987 European Pat. Off. ............ 585/666

Primary Examiner—Anthony McFarlane
Attorney, Agent, or Firm—Alexander J. McKillop; Dennis P. Santini; Laurence P. Hobbes

[57] ABSTRACT

A method is disclosed for the double bond isomerization of alpha olefin-containing feeds, e.g., conversion of 1-butene-containing hydrocarbon streams to 2-butene-rich product streams, wherein oligomer by-products are minimized. The process uses a catalyst composition comprising a zeolite whose surface has been at least partially deactivated for acid catalyzed reactions by chemisorption of a surface-deactivating agent, e.g., collidine, which possesses an average cross section diameter greater than that of the zeolite pores.

18 Claims, No Drawings

DOUBLE BOND ISOMERIZATION OF OLEFIN-CONTAINING FEEDS WITH MINIMAL OLIGOMERTIZATION USING SURFACE ACIDITY DEACTIVATED ZEOLITE CATALYSTS

FIELD OF THE INVENTION

This invention relates to a highly selective method for the double bond isomerization of alpha olefin-containing feeds, e.g., conversion of 1-butene-containing hydrocarbon streams to 2-butene-rich product streams. The process uses a catalyst composition comprising a zeolite whose surface has been at least partially deactivated for acid catalyzed reactions by chemisorption of a surface-deactivating agent which possesses an average cross section diameter greater than that of the zeolite pores.

BACKGROUND OF THE INVENTION

The demand for internal double-bond olefins has recently increased. For example, 2-butene-rich feeds have been found to be useful in the production of alkylate prepared by alkylation of isoparaffins with light olefins. The desirability of using butene-2 as compared to butene-1 as feedstock to an alkylation zone to produce high octane gasoline blending stocks is disclosed in U.S. Pat. No. 2,804,490. U.S. Pat. No. 3,800,003 presents a process in which a feed stream comprising butene isomers is passed into an isomerization zone to increase the quantity of butene-2 available for passage into a downstream alkylation zone. U.S. Pat. No. 4,918,255 discloses an alkylation process using a heterogeneous isoparaffin/olefin alkylation catalyst, e.g. $BF_3/Al_2O_3$, wherein the olefin feed is isomerized to reduce alpha olefin content using as isomerization catalyst alumina, silica, zirconia, chromium oxide, boron oxide, thoria, magnesia, aluminum sulfate or combinations thereof, as well as boron halide-modified metal oxide.

Double bond isomerization of olefins such as butene in the presence of catalysts of the pentasil type such as ZSM-5 and ZSM-11 at temperatures of 100° to 500° C. is disclosed in European Patent Application 0 129 899 to Hoelderich.

European Patent Application 0 247 802 to Barri et al. discloses restructuring olefins using tectometallosilicates of the Theta-1 type (ZSM-22) as well as ZSM-23 at relatively high reaction temperatures of 200° to 550° C. Table 4 thereof shows 1-butene to 2-butene selectivity (mol/mol) of Theta-1 catalyst in the conversion of 1-butene of 92.1% at 234° C. at 100 MPa pressure using an 11.5±2.8% vol/vol 1-butene in nitrogen feed.

U.S. Pat. No. 4,749,819 to Hamilton, Jr. exemplifies double bond isomerization of an alpha olefin feed (preferably $C_{12}$ to $C_{18}$) to produce a product having interior double bond isomerization using a ferrierite catalyst. The reference further teaches at column 5, lines 15 to 19, that "[o]ther aluminosilicates may be exemplified by ZSM-12, ZSM-22, ZSM-23 and ZSM-48."

It is not unexpected that a wide variety of catalysts can be used to isomerize 1-butene at high initial activity inasmuch as the double bond shift is one of the most facile among the hydrocarbon reactions. The thermodynamics of the reaction indicate that enhanced selectivity for 2-butenes occurs at lower temperatures and that relatively great selectivities are possible with a wide variety of catalysts at such temperatures. However, those catalysts which exhibit the desirable activity and stability for the double bond shift reaction can often produce unwanted oligomer by-products.

Accordingly, it would be desirable to provide a method for isomerizing alpha-olefins (or terminal double bond olefins) to internal double bond olefins, e.g, 1-butene feeds to 2-butene rich products, over a catalyst which exhibits high 1-butene conversion and 2-butene selectivity, while minimizing oligomer by-product formation.

It is known in the art that surface acidity of zeolitic catalysts can be modified by treatment with various reagents. U.S. Pat. No. 4,870,038 to Page et al discloses a process for producing substantially linear hydrocarbons by oligomerizing a lower olefin at elevated temperature and pressure with siliceous acidic ZSM-23 whose surface is rendered substantially inactive for acidic reactions, e.g., by contact with 2,4,6-collidine (2,4,6-trimethylpyridine, gamma-collidine). U.S. Pat. No. 5,015,361 to Anthes et al discloses a method for catalytic dewaxing which employs surface acidity deactivated zeolite catalysts. The reduction in surface acidity serves to reduce the amount of lower value cracked products obtained during dewaxing. U.S. Pat. No. 4,101,595 teaches the modification of zeolites by exchange and similar technology with large cations such as $N^+$ and $P^+$ and large branched compounds such as polyamines and the like. Bulky phenolic and silicating zeolite surface-modifying agents are described in U.S. Pat. Nos. 4,100,215 and 4,002,697, respectively. As disclosed in U.S. Pat. Nos. 4,520,221 and 4,568,786, zeolites which have been surface-deactivated by treatment with bulky dialkylamines are useful as catalysts for the oligomerization of lower olefins such as propylene to provide lubricating oil stocks.

As far as is known, surface-deactivated zeolites have heretofore not been used as double-bond isomerization catalysts.

SUMMARY OF THE INVENTION

The present invention relates to a method for isomerizing a terminal double bond olefin-containing organic feedstock to internal double bond olefin which comprises contacting said feedstock under double bond isomerization conditions, with a double bond isomerization catalyst comprising a zeolite whose surface has been at least partially deactivated for acid catalyzed reactions by chemisorption of a surface-deactivating agent which possesses an average cross section diameter greater than that of the zeolite pores. The use of such deactivated catalyst results in reduced oligomerization by-products in the double bond isomerization product stream.

The internal double bond olefin-rich, e.g. 2-butene, stream resulting from the isomerization method of the present invention can be utilized as the olefin stream in isoparaffin-light olefin alkylation. The alkylate made therefrom is an especially valuable component of the gasoline pool as it possesses both high research and motor octane numbers.

The use of a zeolite double bond isomerization catalyst which has been at least partially surface-deactivated in accordance with the invention possesses a decided advantage over the same zeolites the acid sites of which remain substantially intact. In the case of the latter, the acid catalyst activity which is exhibited at the zeolite surface is responsible for an undesirable incidence of oligomerization of olefins, especially iso-olefin, e.g. isobutylene, which decreases the amount of desired internal double bond olefin product resulting from the double bond isomerization operation in which such zeolites are used. In contrast to such unmodified zeolites, the process herein employs a zeolite whose surface acid catalyst activity, and therefore olefin oligomerization activity, has been significantly reduced by treatment with a surface-deactivating agent. Such catalysts also permit the double bond isomerization reaction to take place in the liquid phase while minimizing oligomer make which occurs under the higher pressures associated with liquid phase operation. Finally, such catalysts maintain high activity for an extended period under conditions of low temperature and high pressure. The result, then, in the case of the double bond isomerization process of the present invention is a higher yield of desired internal double-bond olefins and a reduced yield of undesired oligomerized olefin products.

DETAILED DESCRIPTION OF THE INVENTION

The double bond isomerization catalyst which is employed in the process of this invention can be selected from among any of the many zeolites which have heretofore been disclosed as useful for the catalysis of double bond isomerization operations provided its surface acidity has been at least partially reduced by prior and-/or in situ treatment with a surface-deactivating agent, e.g., as disclosed in U.S. Pat. Nos. 4,520,221 and 4,568,786, the contents of which are incorporated by reference herein. Thus, the useful zeolites include one or a combination of the following zeolite double bond isomerization catalysts having a Constraint Index of 1 to 12: ZSM-5, ZSM-11, ZSM-22, ZSM-23, ZSM-35, ZSM-38, and ZSM-48 to name a few.

Zeolite ZSM-5 is described in U.S. Pat. Nos. 3,702,886 and Re. 29,949, the disclosure of which is incorporated by reference herein.

Zeolite ZSM-11 is described in U.S. Pat. No. 3,709,979, the disclosure of which is incorporated by reference herein.

Zeolite ZSM-22 is described in U.S. Pat. No. 4,556,477, the entire contents of which are incorporated herein by reference. ZSM-22 and its preparation in microcrystalline form using ethylpyridinium as directing agent are described in U.S. Pat. No. 4,481,177 to Valyocsik, the entire contents of which are incorporated herein by reference. For purposes of the present invention, ZSM-22 is considered to include its isotypes, e.g., Theta-1, Gallo-Theta-1, NU-10, ISI-1, and KZ-2.

Zeolite ZSM-23 is more particularly described in U.S. Pat. No. 4,076,842, the entire contents of which are incorporated herein by reference.

Zeolite ZSM-35 is described in U.S. Pat. No. 4,016,245, the disclosure of which is incorporated by reference herein.

Zeolite ZSM-48 is described in U.S. Pat. No. 4,397,827, the disclosure of which is incorporated by reference herein.

The extent to which the zeolite can be surface-deactivated can vary over considerable limits, depending on the conditions of the deactivation procedure, and still provide significant improvement over the same zeolite which has not been surface-deactivated. In general, a reduction in surface acid sites on the order of at least about 10%, and preferably at least about 20%, can be readily achieved employing the methods described below.

Deactivation of the surface acid catalytic activity of the selected zeolite can be accomplished in accordance with known and conventional methods. Thus, treatment of the zeolite surface with basic compounds such as amines, phosphines, phenols, polynuclear hydrocarbons, cationic dyes, and the like, will provide the requisite reduction in surface acid catalytic activity.

These surface deactivating agents should have an average cross section diameter of about 5 Angstroms or greater in order to prevent their being sorbed within the zeolite. Examples of suitable amines include monoamines, diamines, triamines, aliphatic and aromatic cyclic amines and heterocyclic amines, porphines, phthalocyanines, 1,10-phenanthroline, 4,7-diphenyl-1,10-phenanthroline, 3,4,7,8-tetramethyl-1,10-phenanthroline, 5,6-benzoquinoline, 2,2':6',2"-terpyridine, 2,4,6-tris(2-pyridyl)-S-triazine and 2,3-cyclododecenopyridine. Examples of phosphines include triphenylphosphine and 1,2-bis(diphenylphosphine)ethane. Suitable phenols are, for example, di-t-butylphenol, alkylated naphthol and 2,4,6-trimethylphenol. Polynuclear hydrocarbons include substances such as pyrene and phenanthrene. Cationic dyes include thionine, methylene blue and triphenylmethane dyes, such as malachite green and crystal violet. Another surface modification technique is deactivation by treating with metal compounds. Suitable metal compounds are magnesium acetate, metal-porphines such as hemin or iron (III) porphine chloride, cobalticinium chloride $(C5H5)_2CoCl$ and titanocene dichloride (biscyclopentadienyl titanium dichloride) and large complex cations such as $[Co(NH_2R)_6]^{2+}$ where R is H or alkyl, $[Pt(NH2R)_4]_{2+}$ where R is alkyl, $[Co(en)_3]^{3+}$ where en is ethylenediamine and manganese (III) meso-tetraphenylporphine.

The zeolites can also be treated with organic silicon compounds as described in U.S. Pat. Nos. 4,100,215 and 4,002,697, the contents of which are incorporated by reference herein, to impart the desired degree of surface deactivation while being essentially free of carbonaceous deposits. Such treatment involves contacting the catalyst with a silane surface-modifying agent capable of deactivating catalytic (acidic) sites located on the external surface of the zeolite by chemisorption. Amines having an average cross section diameter larger than about 5 Angstroms are especially suitable for reducing zeolite surface acid catalysis activity. Examples of such amines include substituted quinolines, heterocyclic amines and alkyl-substituted pyridines such as 2,4 or 1,6-dialkyl pyridines and 2,4,6-trialkyl pyridines. Preferred are bulky, sterically-hindered di-ortho-alkyl pyridines such as 2,6-di-tert-butylpyridine as described in U.S. Pat. Nos. 4,520,221 and 4,568,786 referred to above, and 2,4,6-collidine (2,4,6-trimethyl pyridine, gamma-collidine) as disclosed in U.S. Pat. No. 4,870,038, the contents of which are incorporated herein by reference.

The zeolites of the present invention can be contacted with the surface deactivating agent by adding small amounts of said agent to the feedstock which is to be subjected to double bond isomerization conditions. Suitable amounts of surface deactivating agent in the feed can range from 0.01 to 10 wt. %, preferably 0.5 to 5 wt. %, say, 1 to 3 wt. % of the feedstock. This concentration of deactivating agent in the feed is maintained until the cumulative moles of amine fed per mole of acid $(H^+)$ in the zeolite reaches 0.2 to 0.5. Thereafter the concentration of deactivating agent in the feed is decreased to a maintenance level of 10 to 1000 ppm. The required maintenance level concentration will vary with the amine used and the conditions employed. This level can be adjusted to maintain the desired level of oligomers in the reactor product.

Alternatively, the zeolite can be treated with the agent prior to contact with the organic feedstock. Such treatment can be accomplished by contacting the zeolite with 0.0001 to 1.0 parts by weight, preferably 0.0005 to 0.5 parts by weight, say 0.001 to 0.05 parts by weight of the surface deactivating agent, per weight of zeolite, preferably dissolved in a solvent, e.g. pentane.

The double bond isomerization process of the present invention can be carried out at temperatures of less than 200° C., more preferably 20° to 150° C., say 50° to 130° C.; weight hourly space velocities of the feedstock (based on total feed) between 0.5 and 100 $hr^{-1}$, preferably between 1 and 80 $hr^{-1}$; total pressure between 100 and 10000 kPa, preferably between 300 and 6000 kPa.

Although the present method can be carried out with the feed in the gaseous state, it is preferably carried out in the liquid phase in order to avoid costly and uneconomical vaporization and condensation steps. In order to assure liquid phase operation and to keep the pressure at acceptably low limits, the temperature is preferably kept below the critical temperature of the olefins being treated, which in the case of butenes is about 146° C.

The zeolite catalyst used is preferably at least partly in the hydrogen form, e.g. HZSM-5, HZSM-22, HZSM-23, or HZSM-35. Other metals or cations thereof, e.g. rare earth cations, may also be present. When the zeolites are prepared in the presence of organic cations, they may be quite inactive possibly because the intracrystalline free space is occupied by the organic cations from the forming solution. The zeolite may be activated by heating in an inert atmosphere to remove the organic cations e.g. by heating at over 500° C. for 1 hour or more. The hydrogen form can then be obtained by base exchange with ammonium salts followed by calcination, e.g. at 500° C. in air.

The catalysts employed in the present invention may also contain divalent or trivalent metal cations in amounts ranging from 0 to 3 wt. %, preferably from 0 to 2 wt. %.

The metal may be incorporated into the catalyst by any suitable method such as impregnation or exchange onto the zeolite. The metal may be incorporated in the form of a cationic, anionic or a neutral complex, such as $Pt(NH_3)_4^{2+}$, and cationic complexes of this type are found convenient for exchanging metals onto a zeolite. Anionic complexes are also useful for impregnating metals into the zeolites.

Among the divalent metals suited to incorporation into the catalyst are those of Group IIA, e.g., Mg, Ca and Sr. Suitable trivalent metals include Fe, Al and the lanthanides. Included among the suitable divalent and trivalent metals are the Group VIIIA metals of which the noble metals such as Pd, Pt, Rh and Ru are believed particularly suited to use in the present invention. Among the foregoing metals are those which exhibit hydrogenation ability. Incorporation of hydrogenation metals is particularly useful in carrying out simultaneous butene isomerization and hydrogenation of dienes, e.g. butadiene, or alkynes such as acetylene.

It is generally desirable to incorporate the zeolite with another material resistant to the temperatures and other conditions employed in organic conversion processes. Such matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides. Use of a material in conjunction with the zeolite, i.e. combined therewith, which is active, tends to improve the conversion and/or selectivity of the catalyst in certain organic conversion processes. However, for present purposes, inactive materials of low acidity such as silica or zirconia are preferred in that they prevent unwanted cracking reactions engendered by more active materials such as alumina. Inactive materials can also suitably serve as diluents to control the amount of conversion in a given process so that products can be obtained economically and orderly without employing other means for controlling the rate of reaction.

Frequently, zeolite materials have been incorporated into naturally occurring clays, e.g. bentonite and kaolin. These materials, i.e. clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the zeolite catalyst include the montmorillonite and kaolin family, which families include the sub-bentonites, and the kaolins commonly known as Dixie, McNamee, Georgia and Florida clays or others in which the main mineral constituents is halloysite, kaolinite, dickite, nacrite, or anauxite. Such clays can be used in the raw state as originally mined or initially subjected to calcination, acid treatment or chemical modification.

In addition to the foregoing materials, the zeolite can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

As noted above, of all the foregoing materials, silica is preferred as the matrix material owing to its relative inertness for catalytic cracking reactions which are preferably minimized in the instant isomerization processes. The relative proportions of finely divided zeolite, and inorganic oxide gel matrix vary widely with the zeolite content ranging from about 10 to about 98 percent by weight and more usually in the range of about 50 to about 95 percent by weight of the composite, say about 60 to 90 percent by weight of the composite.

The regeneration of spent zeolite catalyst used in the isomerization reaction is carried out oxidatively or hydrogenatively employing procedures known in the art. The catalyst of the present invention can be readily reactivated without significantly reducing selectivity for isobutene by exposing it to hydrogen for a suitable period, e.g. overnight, and temperature to effect reactivation. For example, the deactivated catalyst is heated in a flowing stream of hydrogen-containing gas to a temperature of 250° C. during 1 hour, and kept at 250° C. for 4 hours. Alternatively, the deactivated catalyst is heated to 350° C. in a flowing stream of inert gas such as nitrogen which contains 0.5% $O_2$ until the major exothermic temperature rise has subsided; the oxygen content is then increased stepwise to 1%, 3%, and finally to about 20%, and the temperature increased to 450° C. and held there for 6 hours.

Alpha value, or alpha number, of a zeolite is a measure of zeolite acidic functionality and is more fully described together with details of its measurement in U.S. Pat. No. 4,016,218, J. Catalysis. 6, pp. 278-287 (1966) and J. Catalysis, 61, pp. 390-396 (1980). The experimental conditions cited in the latter reference are used for characterizing the catalyst described herein. The zeolite catalyst of the present invention has an alpha value ranging from 2 to 300, preferably 5 to 200, based on the zeolite component, when composite catalysts are used.

Feedstream

Suitable organic feeds for the isomerization method of the present invention are those having an average carbon number of about 4 to 5. Such feeds contain 1-olefin, e.g. a $C_3$ to $C_5$ hydrocarbon stream comprising at least 2 wt. % 1-olefin, e.g. at least 2 wt. % 1-butene or at least 2 wt. % 1-pentene. Such feedstocks can include a $C_4$ cut of a cracking process light gas. Such light gas can contain butene isomers in mixture with substantial amounts of paraffins including n-butane and isobutane and preferably contain less than 3 wt. % isobutene. Such $C_4$ cuts can be obtained as the isobutylene-depleted $C_4$ effluent stream of an etherification unit wherein methanol and a catalytic cracking $C_4$ cut are reacted to form methyl tert-butyl ether which is separated from said effluent stream.

Mixtures containing cis-2-butene and trans-2-butene as well as 1-butene can be used. These mixtures can contain the linear butene isomers in a ratio that differs from the thermodynamic equilibrium ratio prevailing at the isomerization reaction temperature. The $C_4$ components usually contain a major amount of unsaturated compounds, such as 5-40% isobutylene, 20-55% linear butenes, and small amounts of butadiene.

The following table lists the thermodynamic linear butene isomer distribution from the thermodynamic data given in *The Chemical Thermodynamics of Organic Compounds*, D. R. Stull, E. F. Westrum, Jr., and G. C. Sinke, John Wiley & Sons, New York, 1969.

TABLE 1

| Temperature, °C. | Percent Composition | |
|---|---|---|
| | 1-Butene | 2-Butene |
| 25 | 2.6 | 97.4 |
| 100 | 6.0 | 94.0 |
| 200 | 10.4 | 89.6 |
| 300 | 15.4 | 84.6 |
| 400 | 20.1 | 79.9 |
| 500 | 24.3 | 75.7 |
| 600 | 28.0 | 72.0 |

The 1-butene-containing feed may also contain 2-butene, isobutylene, n-butane and/or isobutane, as well as $C_1$-$C_3$ and $C_{5+}$ hydrocarbons. In general, it is contemplated to use a stream comprising at least 15%, and preferably at least 25% butenes. Especially preferred feeds are the $C_4$ fractions obtained from catalytic cracking of gas oil, from coking of resid and from steam cracking of naphtha. In one embodiment, the organic feedstock is a $C_4$ cut of a cracking process light gas and contains about 10 wt. % 1-butene.

Two typical compositions of commercial FCC $C_4$ cuts are set out in Table 2 below.

TABLE 2

| | Feed 1 Wt % | Feed 2 Wt % of | | |
|---|---|---|---|---|
| | Total | Total | Olefins | Linear Olefins |
| n-$C_4$ | 19.7 | 6.1 | — | — |
| i-$C_4$ | 46.0 | 29.3 | — | — |
| i-$C_4$= | 5.9 | 19.5 | 30.2 | — |
| 1-$C_4$= | 9.0 | 15.8 | 24.4 | 34.9 |
| 2-tr-$C_4$= | 11.2 | 17.1 | 26.5 | 38.0 |
| 2-cis-$C_4$= | 8.2 | 12.2 | 18.9 | 27.1 |
| | 100.0 | 100.0 | 100.0 | 100.0 |

In view of the desirability of carrying out the isomerization with a feed which comprises minimal isobutene, a preferred feed is the effluent of a liquid phase iso-olefin etherification reactor which employs alkanol and $C_4$ or $C_{4+}$ hydrocarbon feedstock, from which the alkyl tert-butyl ether product is separated out. Inasmuch as isobutene is reacted at nearly quantitative levels in this etherification, the effluent contains only small amounts of isobutene, e.g., less than 3 or even less than 1 wt. % isobutene.

$C_{4+}$ heavier olefinic hydrocarbon streams may be used. Preferred is a $C_5$ cut containing 1-pentene, 2-pentene, isopentene, pentane and isopentane. Other suitable feedstocks include a $C_5$ cut of a cracking process light gasoline, e.g., one containing less than 6% isopentene. The $C_5$ cuts can be obtained as the isopentene-depleted $C_5$ effluent stream of an etherification unit wherein methanol and a catalytic cracking $C_5$ cut are reacted to form methyl tert-amyl ether which is separated from said effluent stream.

U.S. Pat. No. 4,605,787 to Chu et al., provides an example of etherification of isobutene with methanol. It can be carried out in the vapor phase at temperatures between 77° C. and 105° C. in contact with acidic ZSM-5 or ZSM-11 to produce MTBE in high conversion and selectivity. This patent is incorporated herein by reference as an example of suitable effluent which may be employed as feed to the method of the present invention.

In the examples which follow, the isomerization reactions were performed under pressure in the liquid phase in a fixed bed continuous flow reactor. A guard bed consisting of gamma alumina, reduced copper chromite (Oxy-Trap), and molecular sieve Zeolite 4A, was used to eliminate impurities from the $C_4$- mixture feed. The reaction products at various times on stream were analyzed by on-line gas chromatography. Temperatures and flow rates, expressed as WHSV = g feed per g zeolite per hour, are indicated in the tables.

EXAMPLE 1 (COMPARATIVE)

This example is illustrative of the double bond isomerization with an unmodified (non-surface acidity deactivated) ZSM-23/SiO$_2$ catalyst. This catalyst was prepared as follows:

157 parts distilled water were charged to an autoclave, followed by 2.33 parts NaOH solution (50% by weight), 1.0 part aluminum sulfate (17.2% Al$_2$O$_3$), and 1.0 part ZSM-23 seeds (100% basis). After mixing thoroughly, 26.4 parts of precipitated silica (HiSil 233 TM) and then 9.33 parts of pyrrolidine were added and mixed thoroughly. The autoclave was heated to 160° C. with stirring and maintained at these conditions until crystallization was complete. The product was identified as ZSM-23 by X-ray diffraction. After flashing the pyrrolidine, the slurry was cooled, filtered, washed, and dried at 120° C. The catalyst was then exchanged with 1N ammonium nitrate solution (5 ml per gram of catalyst) three times at room temperature for 3 hours. The catalyst was rinsed with deionized/distilled water, dried under flowing air at room temperature, and calcined in nitrogen at 538° C. until all the ammonium was removed.

65 parts of the resulting ZSM-23 product were combined with 20 parts of precipitated silica (Ultrasil VN3SP, 100% solids basis) and 15% colloidal silica (Ludox HS-30). Deionized water was added to give an extrudable mull and the mix extruded to 1/16 inch cylindrical extrudate. The extrudate was dried at 121° C., calcined in nitrogen at 538° C. for 2 hours, and then in air for 3 hours. The extrudate was then exchanged with 1N ammonium nitrate solution (5 ml per gram of catalyst) at room temperature for 1 hour. The exchange was repeated 3 times, the extrudate was rinsed with deionized water, dried at 121° C., and calcined in air at 538° C. for 3 hours. The catalyst was then steamed at 398° C. for 24 hours.

The resulting product, in the form of 14-30 mesh particles, was placed into an electrically heated stainless steel tubular reactor. A simulated alkylation feed from a methyl tert-butyl ether (MTBE) unit containing small amounts of isobutylene having the composition set out in Table 3 was pumped through the reactor in a downflow mode. The product distribution and operating conditions are set out in Table 4 below.

TABLE 3

| Component | Feed Composition | |
|---|---|---|
| | Total | Olefins |
| i-$C_4$° | 47.8 | |
| n-$C_4$=° | 20.8 | |
| i-$C_4$= | 0.4 | 1.3 |
| 1-$C_4$= | 10.0 | 31.8 |
| 2-$C_4$ | 21.0 | 66.9 |

TABLE 4

Product Distribution Obtained Over Unmodified ZSM-23/SiO$_2$

| Operating Conditions | | Olefinic Product Distribution (wt %) | | | |
|---|---|---|---|---|---|
| T(°C.) | WHSV | 1-$C_4$= | 2-$C_4$= | i-$C_4$= | $C_8$=+ |
| 60 | 2.1 | 6.2 | 89.7 | 0.0 | 4.1 |

TABLE 5

| Component | Feed Composition | |
|---|---|---|
| | Total | Olefins |
| i-$C_4$° | 44.1 | |
| n-$C_4$=° | 24.2 | |
| i-$C_4$= | 0.57 | 1.8 |
| 1-$C_4$= | 8.5 | 26.8 |
| 2-$C_4$ | 22.7 | 71.4 |

TABLE 6

Product Distribution Obtained Over Selectivated ZSM-23/SiO$_2$

| Operating Conditions | | Olefinic Product Distribution (wt %) | | | |
|---|---|---|---|---|---|
| T(°C.) | WHSV | 1-$C_4$= | 2-$C_4$= | i-$C_4$= | $C_8$=+ |
| 95 | 1.4 | 6.2 | 90.1 | 1.3 | 2.3 |

TABLE 7

| Component | Feed Composition | |
|---|---|---|
| | Total | Olefins |
| i-$C_4$° | 47.1 | |
| n-$C_4$= | 18.5 | |

TABLE 7-continued

| Component | Feed Composition | |
|---|---|---|
| | Total | Olefins |
| i-$C_4$= | 5.6 | 16.3 |
| 1-$C_4$= | 10.3 | 29.9 |
| 2-$C_4$= | 18.5 | 53.8 |

EXAMPLE 2

A selectivated catalyst was prepared by treating 2.023 g of catalyst of Example 1 with 0.0059 g of 2,4,6-collidine dissolved in pentane. The resulting slurry was thoroughly stirred and heated at about 50° C. until dryness. The resulting catalyst was used in a double bond isomerization process using a feed similar to that of Example 1. The composition of the feed is set out below in Table 5. The product distribution and operating conditions are set out in Table 6 below. Comparison of the product distributions of the double bond isomerization products of Examples 1 and 2 indicate that the selectivation treatment of the ZSM-23/SiO$_2$ catalyst is effective in reducing the undesired formation of oligomers ($C_8$+). Example 1 shows that on the unmodified ZSM-23/SiO$_2$ catalyst, all the isobutylene reacted to produce oligomers, while on the collidine modified ZSM-23/SiO$_2$ catalyst of Example 2, only 28% of the isobutylene was consumed, with a corresponding reduction in the amount of undesirable oligomer formed.

EXAMPLE 3 (COMPARATIVE)

The feed used in this example was a simulated FCC $C_4$— cut, that contains about 16 wt. % isobutylene having the composition set out in Table 7. The catalyst employed was an unmodified ZSM-23/SiO$_2$ prepared as in Example 1. The product distribution and operating conditions are set out in Table 8 below.

TABLE 8

Product Distribution Obtained Over Unmodified ZSM-23/SiO$_2$

| Operating Conditions | | Olefinic Product Distribution (wt %) | | | |
|---|---|---|---|---|---|
| T(°C.) | WHSV | 1-$C_4$= | 2-$C_4$50 | i-$C_4$= | $C_8$== |
| 80 | 6.1 | 5.0 | 70.5 | 0.2 | ~24.2 |

EXAMPLE 4

A selectivated catalyst was prepared as set out in Example 2. The resulting catalyst was used in a double bond isomerization process using the feed of Example 3. The product distribution and operating conditions are set out in Table 9 below.

TABLE 9

Product Distribution Obtained Over Selectivated ZSM-23/SiO$_2$

| Operating Conditions | | Olefinic Product Distribution (wt %) | | | |
|---|---|---|---|---|---|
| T(°C.) | WHSV | 1-$C_4$= | 2-$C_4$= | i-$C_4$= | $C_8$=+ |
| 95 | 0.85 | 5.8 | 74.3 | 9.8 | ~10.1 |

Comparison of the product distributions of the double bond isomerization products of Examples 3 and 4 indicate that the selectivation treatment of the ZSM-23/SiO$_2$ catalyst is effective in reducing the undesired formation of oligomers ($C_8$+), even where the feed contains significant amounts of isobutylene.

We claim:

1. A method for double bond isomerization of alpha-olefin-containing organic feedstock with minimal oligomerization which comprises contacting said feedstock under double bond isomerization conditions with a double bond isomerization catalyst comprising a zeolite having a Constraint Index of 1 to 12 whose surface has been at least partially deactivated for acid catalyzed reactions by chemisorption of an alkyl-substituted pyridine surface-deactivating agent which possesses an average cross section diameter greater than that of the zeolite pores.

2. The method of claim 1 wherein said isomerizing is carried out at temperatures of less than 200° C., weight hourly space velocities of the feedstock (based on total feed) between 0.5 and 100 hr$^{-1}$, and total pressure between 100 and 10000 kPa.

3. The method of claim 1 wherein said isomerizing is carried out in the liquid phase at temperatures of 20° to 150° C., weight hourly space velocities of the feedstock (based on total feed) between 1 and 80 hr$^{-1}$; and total pressure between 300 and 6000 kPa.

4. The method of claim 1 wherein said isomerizing is carried out in the liquid phase.

5. The method of claim 1 wherein said zeolite has the framework structure of a zeolite selected from the group consisting of ZSM-5, ZSM-11, ZSM-22, ZSM-23, ZSM-35, ZSM-38 and ZSM-48.

6. The method of claim 1 wherein said zeolite has the structure of ZSM-5.

7. The method of claim 1 wherein said zeolite has the structure of ZSM-22.

8. The method of claim 1 wherein said zeolite has the structure of ZSM-23.

9. The method of claim 1 wherein said catalyst comprises 2 to 90 wt. % of a matrix selected from the group consisting of silica, alumina, and silica-alumina.

10. The method of claim 1 wherein said catalyst comprises 5 to 50 wt. % of a silica matrix.

11. The method of claim 1 wherein said surface-deactivating agent is 2,4,6-collidine.

12. The method of claim 1 wherein said surface-deactivating agent is added to said organic feedstock.

13. The method of claim 1 wherein said zeolite is contacted with 0.0001 to 1.0 parts by weight of said surface-deactivating agent per weight of said zeolite.

14. The method of claim 1 wherein said zeolite is contacted with 0.001 to 0.05 parts by weight of said surface-deactivating agent per weight of said zeolite.

15. The method of claim 1 wherein said organic feedstock comprises $C_4$ to $C_{12}$ olefins.

16. The method of claim 1 wherein said organic feedstock is a $C_3$ to $C_5$ hydrocarbon stream comprising at least 10 wt. % 1-butene.

17. The method of claim 1 wherein said organic feedstock is a $C_4$-cut of a cracking process light gas.

18. The method of claim 1 wherein said zeolite has the structure of ZSM-35.

* * * * *